United States Patent
Hessels et al.

(10) Patent No.: US 10,329,625 B2
(45) Date of Patent: Jun. 25, 2019

(54) METHOD FOR DETECTING DLX1 MRNA, HOXC6 MRNA, AND KLK3 MRNA IN A URINE SAMPLE AND PREDICTING AND TREATING CLINICALLY SIGNIFICANT PROSTATE CANCER

(71) Applicant: MDxHealth Research B.V., Nijmegen (NL)

(72) Inventors: Daphne Hessels, Nijmegen (NL); Franciscus Petrus Smit, Nijmegen (NL); Jack A. Schalken, Nijmegen (NL)

(73) Assignee: MDxHealth Research B.V., Nijmegen (NL)

( * ) Notice: Subject to any disclaimer, the term of this patent is extended or adjusted under 35 U.S.C. 154(b) by 0 days.

(21) Appl. No.: 15/357,342

(22) Filed: Nov. 21, 2016

(65) Prior Publication Data
US 2017/0145518 A1 May 25, 2017

Related U.S. Application Data

(60) Provisional application No. 62/258,163, filed on Nov. 20, 2015.

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| 2012/0108453 A1 | 5/2012 | Smit et al. |
| 2014/0073535 A1 | 3/2014 | Smit |
| 2014/0106363 A1 | 4/2014 | Smit |
| 2015/0017640 A1 | 1/2015 | Smit et al. |
| 2016/0194724 A1 | 7/2016 | Smit et al. |

FOREIGN PATENT DOCUMENTS

| WO | 2010037735 A1 | 4/2010 |
| WO | 2012152800 A1 | 11/2012 |
| WO | 2012152811 A1 | 11/2012 |
| WO | 2013064636 A1 | 5/2013 |
| WO | 2014135698 A2 | 9/2014 |
| WO | 2015022164 A1 | 2/2015 |

OTHER PUBLICATIONS

Hendricks et al (Abstract POO3 "Validation of a new urine test for the early diagnosis of clinically significant prostate cancer" European Urology Supplements vol. 14, No. 7, 2015, pp. 149-221). (Year: 2015).*
Albertsen et al. "20-year outcomes following conservative management of clinically localized prostate cancer", Jama. 2005;293:2095-101.
Auprich et al. "Critical assessment of preoperative urinary prostate cancer antigen 3 on the accuracy of prostate cancer staging", European urology. 2011;59:96-105.
Baco et al. "A Randomized Controlled Trial to Assess and Compare the Outcomes of Two-core Prostate Biopsy Guided by Fused Magnetic Resonance and Transrectal Ultrasound Images and Traditional 12-core Systematic Biopsy", European urology. 2015, http://dx.doi.org/10.1016/j.eururo.2015.03.041.
Budaus et al. "Initial Experience of Ga-PSMA PET/CT Imaging in High-risk Prostate Cancer Patients Prior to Radical Prostatectomy" European urology. 2015, http://dx.doi.org/10.1016/j.eururo.2015.06.010.
Bussemakers et al. "DD3: a new prostate-specific gene, highly overexpressed in prostate cancer. Cancer research", 1999;59:5975-9.
Draisma et al. "Lead time and overdiagnosis in prostate-specific antigen screening: importance of methods and context", Journal of the National Cancer Institute. 2009;101:374-83.
Gittelman et al. "PCA3 molecular urine test as a predictor of repeat prostate biopsy outcome in men with previous negative biopsies: a prospective multicenter clinical study", The Journal of urology. 2013;190:64-9.

(Continued)

*Primary Examiner* — Catherine S Hibbert
(74) *Attorney, Agent, or Firm* — Quarles & Brady LLP

(57) ABSTRACT

The present invention relates to methods, devices, combinations, kits, and systems for predicting and treating clinically significant prostate cancer in a urine sample of an individual suspected of suffering from prostate cancer based on expression analysis of normalized prostate tumor markers. The present methods, devices, combinations, kits, and systems are especially suitable for predicting and treating prostate cancer with a Gleason score of seven or more in individuals with a serum prostate-specific antigen (sPSA) level lower than 15 ng/ml. Specifically, the present invention relates to methods, devices, combinations, kits, and systems for predicting and treating clinically significant prostate cancer in a urine sample of an individual suspected of suffering from prostate cancer, the method comprises the steps of: a) determining mRNA expression levels of one or more of the genes DLX1, HOXC6, TDRD1 and KLK3 in a urine sample of said individual; b) normalizing the mRNA expression levels of one ore more of DLX1, HOXC6, and TDRD1 using the mRNA expression level of KLK3; and c) establishing clinically significant prostate cancer based on a combination of the KLK3 normalized expression levels of the combination of one or more of DLX1, HOXC6, and TDRD1. Treatment for prostate cancer may be administered based on the expression levels of one or more of DLX1, HOXC6, and TDRD1.

8 Claims, 5 Drawing Sheets

(56) References Cited

OTHER PUBLICATIONS

Groskopf et al. "APTIMA PCA3 molecular urine test: development of a method to aid in the diagnosis of prostate cancer", Clinical chemistry. 2006;52:1089-95.

Hendriks et al. "Comparative analysis of prostate cancer specific biomarkers PCA3 and ERG in whole urine, urinary sediments and exosomes", Submitted. 2015.

Hessels et al. "DD3(PCA3)-based molecular urine analysis for the diagnosis of prostate cancer", European urology. 2003;44:8-15; discussion-6.

Hoeks et al. "Prostate cancer: multiparametric MR imaging for detection, localization, and staging", Radiology. 2011;261:46-66.

Leyten et al. "Identification of a Candidate Gene Panel for the Early Diagnosis of Prostate Cancer", Clinical cancer research: an official journal of the American Association for Cancer Research. 2015;21:3061-70.

Marks et al. "PCA3 molecular urine assay for prostate cancer in men undergoing repeat biopsy", Urology. 2007;69:532-5.

Ploussard et al. "The prostate cancer gene 3 (PCA3) urine test in men with previous negative biopsies: does free-to-total prostate-specific antigen ratio influence the performance of the PCA3 score in predicting positive biopsies?" BJU international. 2010;106:1143-7.

Roehl et al. "Serial biopsy results in prostate cancer screening study", The Journal of urology. 2002;167:2435-9.

Schmittgen et al. "Analyzing real-time PCR data by the comparative C(T) method", Nature protocols. 2008;3:1101-8.

Thompson et al. "Assessing prostate cancer risk: results from the Prostate Cancer Prevention Trial", Journal of the National Cancer Institute. 2006;98:529-34.

Thompson et al. "Prevalence of prostate cancer among men with a prostate-specific antigen level < or =4.0 ng per milliliter", The New England journal of medicine. 2004;350:2239-46.

Tonttila et al. "Prebiopsy Multiparametric Magnetic Resonance Imaging for Prostate Cancer Diagnosis in Biopsy-naive Men with Suspected Prostate Cancer Based on Elevated Prostate-specific Antigen Values: Results from a Randomized Prospective Blinded Controlled Trial", European urology. 2015, http://dx.doi.org/10.1016/j.eururo.2015.05.024.

Torre et al. "Global cancer statistics", 2012. CA: a cancer journal for clinicians. 2015;65:87-108.

Welch et al. "Prostate cancer diagnosis and treatment after the introduction of prostate-specific antigen screening: 1986-2005", Journal of the National Cancer Institute. 2009;101:1325-9.

Wolters et al. "False-negative prostate needle biopsies: frequency, histopathologic features, and follow-up", The American journal of surgical pathology. 2010;34:35-43.

Leyten, et al., "Identification of a Candidate Gene Panel for the Early Diagnosis of Prostate Cancer", Clin Cancer Res; 21(13) Jul. 1, 2015, pp. 3061-3071.

International Search Report and Written Opinion for PCT/IB16/001763 dated Feb. 23, 2017.

Hendriks, R., et al., "SIU 2015 Abstracts Book", World J. of Urology, Springer International DE, MP-03.01 and MP-03.02, Oct. 16, 2015, p. 10.

International Preliminary Report on Patentability for PCT/IB2016/001763 dated May 22, 2018.

\* cited by examiner

METHOD FOR DETECTING DLX1 MRNA, HOXC6 MRNA, AND KLK3 MRNA IN A URINE SAMPLE AND PREDICTING AND TREATING CLINICALLY SIGNIFICANT PROSTATE CANCER

CROSS-REFERENCE TO RELATED PATENT APPLICATIONS

The present application claims the benefit of priority under 35 U.S.C. 119(e) to U.S. Provisional Patent Application No. 62/258,163, filed on Nov. 20, 2016, the content of which is incorporated herein by reference in its entirety.

BACKGROUND

The present invention relates to methods for predicting clinically significant prostate cancer in a biopsy using a urine sample of an individual suspected of suffering from prostate cancer. It is based on expression analysis of normalised prostate tumour markers. The present methods are especially suitable for predicting prostate cancer with a Gleason score of seven or more in individuals with a serum prostate-specific antigen (sPSA) level lower than 15 ng/ml. The present invention further relates to kits of parts for predicting clinically significant prostate cancer in a urine sample based on expression analysis and to the use of normalised prostate tumour markers for detecting prostate cancer in a urine sample.

Worldwide, prostate cancer or PCa is the second most frequently diagnosed cancer among men, with 1.1 million estimated new cases and 307.500 estimated deaths in 2012. Since the introduction of serum prostate-specific antigen (sPSA) testing, the incidence of PCa has increased. However, sPSA-testing has also led to an increased amount of unnecessary biopsies and diagnosis of clinically insignificant tumors which would not have been life-threatening (potential overtreatment); especially in the sPSA 'grey-zone' (4.0-10.0 ng/ml) where 65-70% of men have a negative biopsy result. Men with indolent disease, who undergo treatment, may suffer complications without a reduction in their risk of dying from PCa. Generally, men with high-grade PCa have a high probability of dying from PCa within 10 years, whereas men with low-grade PCa have a minimal risk of dying from this disease.

The major challenge is to improve the detection of clinically significant or high-grade PCa in an early stage. Both overdiagnosis and overtreatment could be reduced if PCa-specific biomarkers could distinguish indolent from aggressive tumors. Ideally the biomarkers could be measured in a sample that can be obtained non-invasively, for example in urine.

The Prostate CAncer gene 3 (PCA3)-based urinary test (Progensa® PCA3, GenProbe) is the only FDA-approved molecular diagnostic test for the detection of PCa in urine. PCA3 was identified as a gene encoding a long non-coding RNA that was consistently upregulated in PCa. PCA3 was shown to be of value in PCa detection, however, the relation with tumor aggressiveness and thus prognostic value remains controversial.

A stepwise approach for the identification and selection of new biomarkers using gene expression profiling has been suggested. A gene panel measured in urinary sediments predicted Gleason score ≥7 upon prostate biopsy. The test, based on mRNA levels of Homeobox C6 (HOXC6), Distal-less Homeobox 1 (DLX1), and Tudor domain containing 1 (TDRD1), was shown to have independent additional value to sPSA for predicting high-grade PCa upon biopsy. The combination of HOXC6, DLX1, and TDRD1 outperformed Progensa® PCA3. Furthermore, the predictive accuracy could be improved when urinary HOXC6, DLX1, and TDRD1 were combined with sPSA. HOXC6, DLX1, and TDRD1 are upregulated in PCa and these genes may be involved in the onset of PCa and are associated with high-grade PCa. However, although the test showed promising results when performed on a urine sediment sample, analysis of whole urine samples were not satisfactory.

SUMMARY

Considering the above, there is an urgent clinical unmet need in the art for new biomarkers that can predict high-grade disease to aid in decision making regarding further diagnostic evaluations (for example prostate biopsies or imaging) and treatment.

It is an object of the present invention, amongst other objects, to meet the above need in the art.

According to the invention this object is met, amongst other objected as outlined in the appended claims.

Specifically, this object, amongst other objects, is, according to a first aspect, met by method for predicting clinically significant prostate cancer in a urine sample of an individual suspected of suffering from prostate cancer, the methods comprise the steps of:

a1) determining mRNA expression levels of one or more of the genes DLX1, HOXC6, TDRD1, and KLK3 in a urine sample of said individual;

b1) normalizing the mRNA expression levels of one or more of DLX1, HOXC6, and TDRD1 using the mRNA expression level of KLK3 (e.g., by dividing the expression levels of one or more of DLX1, HOXC6, and TDRD1 by the mRNA expression level of KLK3);

c) establishing clinically significant prostate cancer based on a combination of the KLK3 normalized expression levels of the combination of DLX1 and HOXC6 and optionally TDRD1.

DLX1 belongs to the family of homeodomain transcription factors which are related to the *Drosophila* distal-less (Dll) gene. The family has been related to a number of developmental features and appears to be well preserved across species. Dlx genes are implicated in tangential migration of interneurons from the subpallium to the pallium during vertebrate brain development. It has been suggested that Dlx promotes the migration of interneurons by repressing a set of proteins that are normally expressed in terminally differentiated neurons and act to promote the outgrowth of dendrites and axons.

With respect to DLX1 expression, at least two transcript variants are known. Transcript variant 1 is longer than transcript variant 2 and contains an internal exon in the coding region that results in a frame shift and premature stop codon. Within the context of the present invention, DLX1 expression level determination refers to determination of the expression levels of both transcripts.

HOXC6 is a family member of the homeobox superfamily of genes and the HOX subfamily contain members that are transcription factors involved in controlling and coordinating complex functions during development via spatial and temporal expression patterns. In humans, there are 39 classical HOX genes organized into the clusters A, B, C and D.

Three genes, HOXC4, HOXC5 and HOXC6, share a 5' non-coding exon. Transcripts may include the shared exon spliced to the gene-specific exons, or they may include only the gene-specific exons. For HOXC6, alternatively spliced transcript variants encoding different isoforms have been identified. Transcript variant two represents the longer transcript and includes the shared exon. It contains a distinct 5'UTR and lacks an in-frame portion of 5' coding region compared to variant one. The resulting isoform two has a shorter N-terminus when compared to isoform one. Transcript variant one includes only gene-specific exons and encodes the longer isoform. Within the context of the present invention, HOXC6 expression level determination refers to the expression levels of variants 1 and 2.

Prostate-specific antigen (PSA), also known as gamma-semino protein or kallikrein-3 (KLK3), is a glycoprotein enzyme encoded by the KLK3 gene. KLK3 is a member of the kallikrein-related peptidase family and is secreted by the epithelial cells of the prostate gland. KLK3 is produced for the ejaculate, where it liquefies semen in the seminal coagulum and allows sperm to swim freely. KLK3 is present in small quantities in the serum of men with healthy prostates, but is often elevated in the presence of prostate cancer or other prostate disorders.

It is noted that the United States Preventive Services Task Force (USPSTF, 2012) does not recommend PSA screening, noting that the test may result in "overdiagnosis" and "overtreatment" because "most prostate cancer is asymptomatic for life" and treatments involve risks of complications including impotence (erectile dysfunction) and incontinence. The USPSTF concludes "the potential benefit does not outweigh the expected harms." Approximately 30 percent of patients with high KLK3 have prostate cancer diagnosed after biopsy.

According to a preferred embodiment, the present mRNA expression levels of DLX1 and HOXC6 and optionally TDRD1 are normalised by calculating the ratio between DLX1 mRNA, HOXC6 mRNA and optionally TDRD1 mRNA and the expression level of KLK3 mRNA.

According to another preferred embodiment, the present mRNA expression levels are determined using a quantitative Polymerase Chain Reaction (qPCR). The use of qPCR allows for, when determining mRNA expression levels, to measure the crosspoint cycle (Cp), i.e. the cycle wherein the detection signal crosses a predetermined threshold. The Cp value inversely correlates with the initial concentration of the mRNA, e.g. the lower the Cp the higher the gene expression in the sample. The Cp values and copy numbers of the present target genes allows for calculating the present ratios to normalize the qPCR results relative to a reference level for example by using the Delta DeltaCp method ($\Delta\Delta Cp$):

$$\text{Ratio} = 2\left(\left(AvgCp_{(Cal10^4)_{target}} - Cp_{(sample)_{target}}\right) - \left(AvgCp_{(Cal10^4)_{reference}} - Cp_{(sample)_{reference}}\right)\right) \times 10.000$$

A suitable reference level for normalizing the expression levels of a target (e.g., DLX1, HOXC2, and/or TDRD1 mRNA) may include the expression level of KLK3 mRNA.

According to the present invention, a clinically significant prostate cancer preferably is high-grade prostate cancer or prostate cancer with a Gleason score of 7 or higher. The Gleason grading system is generally used to evaluate the prognosis of men with prostate cancer using samples from a prostate biopsy. Together with other parameters, it is incorporated into a strategy of prostate cancer staging which predicts prognosis and helps guide therapy. A Gleason score is given to prostate cancer based upon its microscopic appearance. Cancers with a higher Gleason score are more aggressive and have a worse prognosis.

According to yet another preferred embodiment, the present method is used for predicting clinically significant prostate cancer in a urine sample of an individual having a serum prostate-specific antigen (sPSA) level lower than 15 ng/ml, preferably lower than 10 ng/ml. Especially in this group of individuals, the chance of "overdiagnosis" and "overtreatment" is relatively high According to still another preferred embodiment, the present method further comprises
 a) determining mRNA expression levels of the genes HOXC4 and/or TDRD1 in a urine sample of said individual;
 b) normalizing the mRNA expression levels of HOXC4 and/or TDRD1 using the mRNA expression level of KLK3; and
step c comprises establishing clinically significant prostate cancer based on a combination of the KLK3 normalized expression levels of the combination of DLX1 and HOXC6 and HOXC4 and/or TDRD1.

The present determining mRNA expression levels preferably comprises isolating mRNA from a urine sample preferably a first voided urine sample.

According to a second aspect, the present invention relates to kit of parts for predicting clinically significant prostate cancer comprising:
 1) one or more means for collecting urine;
 2) means for isolating mRNA from urine; and
 3) means for determining mRNA expression levels of the genes DLX1, HOXC6 and KLK3.

And, according to a third aspect, to the use of mRNA expression levels of HOXC6 and DLX1 and optionally TDRD1 in a urine sample for predicting clinically significant prostate cancer wherein said mRNA expression levels of HOXC6 and DLX1 and optionally TDRD1 are normalised against KLK3 mRNA expression levels.

The foregoing methods further may include performing the foregoing methods to determine the mRNA expression levels of the genes DLX1 and HOXC6 and optionally TDRD1 in a urine sample and/or requesting a test providing results of an analysis to determine the mRNA expression levels of the genes DLX1 and HOXC6 and optionally TDRD1 in a urine sample. In addition, the foregoing methods may include performing further diagnostic tests and/or requesting results of further diagnostic tests, based on the detected mRNA expression levels of HOXC6 and/or DLX1 and/or TDRD1 (e.g., based on detecting elevated or reduced expression levels of HOXC and/or DLX1 and/or TDRD1 relative to a normal control which may include nucleic acid isolated from urine of a patient not having prostate cancer). Further, the foregoing methods may include administering therapy for prostate cancer based on the detected mRNA expression levels of HOXC6 and/or DLX1 and/or TDRD1 (e.g., based on detecting elevated or reduced expression levels of HOXC and/or DLX1 and/or TDRD1 relative to a normal control which may include nucleic acid isolated from urine of a patient not having prostate cancer).

The disclosed methods may be performed utilizing devices, combinations, kits, and systems that comprise or utilize components for detecting mRNA expression levels of one or more of HOXC6, DLX1, TDRD1 and/or KLK3 in a urine sample. In addition, the disclosed methods may be performed utilizing devices, combinations, kits, and systems that comprise or utilize components for treating prostate cancer based the detected mRNA expression levels of one or more of HOXC6, DLX1, TDRD1 and/or KLK3 in a urine sample.

BRIEF DESCRIPTION OF THE FIGURES

The present invention will be further detailed in the following example of an especially preferred embodiment of the present invention. In the example, reference is made to figures wherein.

DETAILED DESCRIPTION

Figure 1:
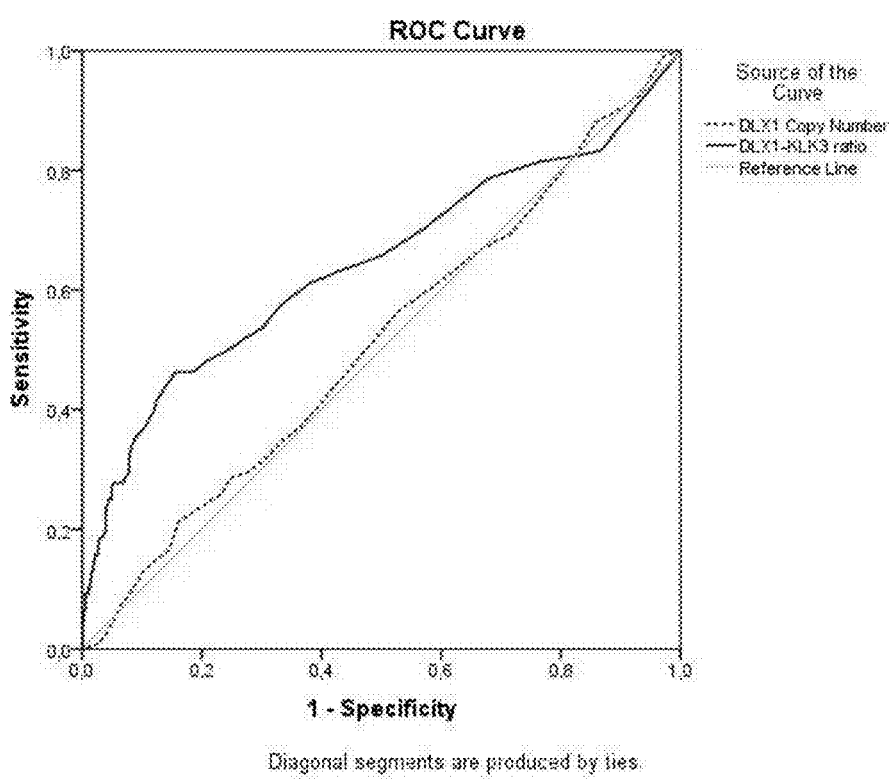
FIG. 1: shows the ROC curves for the prediction of high grade PCa upon prostate biopsy: (1) DLX1/KLK3 ratio (black solid line; AUC 0.64 [95% CI: 0.58-0.71]); (2) DLX1 copy number (grey dotted line; AUC 0.51 [95% CI: 0.45-0.58])

Disclosed are methods, devices, combinations, kits, and systems for diagnosing and treating prostate cancer. The methods, devices, combinations, kits, and systems are described herein using several definitions, as set forth below and throughout the application.

As used in this specification and the claims, the singular forms "a," "an," and "the" include plural forms unless the context clearly dictates otherwise. For example, "a component" should be interpreted to mean "one or more components" unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The presently disclosed methods, devices, combinations, kits, and systems relate to detecting elevated expression of mRNA of the genes DLX1 and/or HOXC6 in a urine sample in order to diagnose and/or prognose an individual, and optionally treat the diagnosed and/or prognosed individual by administering therapy to the individual for treating prostate cancer based on the genetic marker having been identified. Elevated expression of mRNA of the genes DLX1 and/or HOXC6 may be identified relative to an internal control (e.g., expression of mRNA of the gene KLK3) and/or relative to an external control (e.g., expression of mRNA of the genes DLX1 and/or HOXC6 in a patient not having prostate cancer). Expression of mRNA of the genes DLX1 and/or HOXC6 in a urine sample may be normalized relative to expression of mRNA of the gene KLK3 in the urine sample and a HOXC6-DLX1 score may be calculated as disclosed herein (e.g., a HOXC6-DLX1 score of at least about 5, 10, 20, 30, 40, 50, 60, 70, 80, 90, 100, 110, 120, 130, 140, 150, 160, 170, 180, 190, 200 or higher). Further diagnostics may be performed on a sample from the individual based on the HOXC6-DLX1 score (e.g., a Gleason score on a prostate biopsy from the patient) and/or therapy may be administered to the patient based on the HOXC6-DLX1 score. A HOXC6-DLX1 score may be generated by determining the area under the curve (AUC) of a Receiver Operating Characteristic (ROC) curve and corresponding 95% confidence intervals (CI).

Optionally, the presently disclosed methods, devices, combinations, kits, and systems may relate to detecting elevated expression of mRNA of the genes DLX1, HOXC6, and/or TDRD1 in a urine sample in order to diagnose and/or prognose an individual, and optionally treat the diagnosed and/or prognosed individual by administering therapy to the individual for treating prostate cancer based on the genetic marker having been identified. Elevated expression of mRNA of the genes DLX1, HOXC6, and/or TDRD1 may be identified relative to an internal control (e.g., expression of mRNA of the gene KLK3) and/or relative to an external control (e.g., expression of mRNA of the genes DLX1, HOXC6, and/or TDRD1 in a patient not having prostate cancer). Expression of mRNA of the genes DLX1, HOXC6, and/or TDRD1 in a urine sample may be normalized relative to expression of mRNA of the gene KLK3 in the urine sample and a HOXC6-DLX1-TDRD1 score may be calculated as disclosed herein (e.g., a HOXC6-DLX1-TDRD1 score of at least about 5, 10, 20, 30, 40, 50, 60, 70, 80, 90, 100, 110, 120, 130, 140, 150, 160, 170, 180, 190, 200 or higher). Further diagnostics may be performed on a sample from the individual based on the HOXC6-DLX1-TDRD1 score (e.g., a Gleason score on a prostate biopsy from the patient) and/or therapy may be administered to the patient based on the HOXC6-DLX1-TDRD1 score. A HOXC6-DLX1-TDRD1 score may be generated by determining the area under the curve (AUC) of a Receiver Operating Characteristic (ROC) curve and corresponding 95% confidence intervals (CI).

As used herein, the term "individual," which may be used interchangeably with the terms "patient" or "subject," refers to one who receives medical care, attention or treatment and may encompass a human patient. As used herein, the term "individual" is meant to encompass a person who has a prostate cancer, is suspected of having prostate cancer, or is at risk for developing a prostate cancer. Suitable individuals may include, but are not limited to, individuals having a serum prostate-specific antigen (sPSA) level of at least about 0.1, 0.5, 1, 2, 3, 4, 5, 6, 7, 8, 9, 10, 11, 12, 13, 14, or 15 ng/ml, or individuals having a sPSA level within a range bounded by any of 0.1, 0.5, 1, 2, 3, 4, 5, 6, 7, 8, 9, 10, 11, 12, 13, 14, or 15 ng/ml (e.g., individuals having a sPSA level within a range of 4-10 ng/ml). The presently disclosed methods, devices, combinations, kits, and systems may relate to detecting elevated sPSA in a sample from an individual.

The term "sample" should be interpreted to include, but not be limited to, bodily fluids (e.g., blood products including serum) and urine, as well as tissue samples (e.g., a prostate biopsy). The term sample should be interpreted to include, but not be limited to, serum samples having a serum prostate-specific antigen (sPSA) level of at least about 0.1, 0.5, 1, 2, 3, 4, 5, 6, 7, 8, 9, 10, 11, 12, 13, 14, or 15 ng/ml, or serum samples having a sPSA level within a range bounded by any of 0.1, 0.5, 1, 2, 3, 4, 5, 6, 7, 8, 9, 10, 11, 12, 13, 14, or 15 ng/ml (e.g., serum samples having a sPSA level within a range of 4-10 ng/ml).

The disclosed methods, devices, combinations, kits, and systems may include or utilize means and/or components for detecting mRNA, including, but not limited to mRNA of the genes DLX1, HOXC6, TDRD1, and/or KLK3. Means and components may include, but are not limited to one or more oligonucleotides that hybridize to mRNA, including, but not limited to mRNA of the genes DLX1, HOXC6, TDRD1, and/or KLK3 or that hybridize to reverse transcribed mRNA (e.g., cDNA), including but not limited to cDNA of the genes DLX1, HOXC6, TDRD1, and/or KLK3. Oligonucleotides may include a DNA primer form reverse transcribing mRNA, including, but not limited to mRNA of the genes DLX1, HOXC6, TDRD1 and/or KLK3. Oligonucleotides may include a pair of DNA primers for amplifying reverse transcribed mRNA (e.g., cDNA), including but not limited to cDNA of the genes DLX1, HOXC6, TDRD1 and/or KLK3 Means and components may include enzymes for reverse transcribing mRNA (e.g., a reverse transcriptase which optionally may be stable at temperatures >70° C.) and/or enzymes for amplifying reverse transcribed mRNA (i.e., DNA polymerases which optionally may be stable at temperature >70° C.).

The disclosed methods, devices, combinations, kits, and systems may include or utilize therapies or therapeutic agents for treating prostate cancer. Therapies for prostate cancer may include, but are not limited to performing surgery (e.g., surgery to remove cancerous prostate tissue), administering radiation therapy (e.g., radiation therapy directed at cancerous prostate tissue), administering radiopharmaceutical therapy (e.g., administering radiopharmaceuticals such as radio-labelled antibodies directed against cancerous prostate tissue), administering hormone therapy (e.g. administering anti-androgen therapy), administering chemotherapy, administering biologic therapy, administering bisphosphonate therapy, administering cryotherapy (e.g., cryotherapy directed against the cancerous prostate tissue), administering high-intensity focused ultrasound therapy (e.g., high-intensity focused ultrasound therapy directed against the cancerous prostate tissue), administering proton beam radiation therapy (e.g., proton beam radiation therapy directed against the cancerous prostate tissue), or a combination thereof.

The disclosed methods, devices, combinations, kits, and systems and may incorporate methods, devices, combinations, kits, and systems a known in the art. (See, e.g., WO 2010/037735; WO 2012/152811; WO2013/064636; and WO 2015/022164; the contents of which are incorporated herein by reference in their entireties.

Example

This example shows the validation of a gene panel based mRNA test performed on whole urine, and a predictive model (using biomarkers HOXC6, DLX1, TDRD1, and HOXC4) useful for identifying patients with high-grade PCa (Gleason score ≥7) upon prostate biopsy.

Material and Methods

Study Population

In two prospective multicenter studies, men who were scheduled for (initial or repeat) prostate biopsies, based on an elevated sPSA levels (≥3 ng/ml), an abnormal DRE and/or a family history of PCa were consecutively included. Urine samples were collected after a standardized DRE. Subjects were enrolled from six urology clinics in the Netherlands between September 2009 and July 2011 (Clinical trial A) and between July 2011 and September 2014 (Clinical trial B). Exclusion criteria were: history of PCa, medical therapy known to affect sPSA levels, prostate biopsy within three months prior to enrolment, and invasive treatment for benign prostate hyperplasia (BPH) within six months prior to enrolment. Transrectal ultrasound (TRUS) guided prostate biopsy (median of 10 cores) were performed and evaluated per hospital's standard procedure and by local pathologists. Institutional Review Boards of all hospitals approved the study protocols and written informed consent was obtained from each participant. Test results were not provided to the clinical sites for patient care and the laboratory technicians that performed the biomarker tests were blinded for patient characteristics.

Sample Collection and Processing

Approximately 30 ml of first voided urine was collected in a collection cup after DRE. After collection, the urine was immediately transferred into a urine specimen transport tube (Gen-Probe, Hologic). The samples were shipped at room temperature to a central laboratory, and were stored within 7 days at −80° C.

Laboratory Developed Test (LDT) Development

In the discovery and initial validation study urinary sediments were used; we subsequently developed and standardized the assay using fixed whole urine as substrate. The assays were performed using the prototype amplification kit (Labo Bio-medical Products BV, LBP). In short, RNA was isolated out of 1 ml of urine using the MagNAPure 96 instrument (Roche). Subsequently, the RNA levels of HOXC4, HOXC6, TDRD1, DLX1, KLK3 and PCA3 were determined using one-step reverse transcription quantitative PCR (RT-qPCR).

Next to the expression levels (copy numbers) of the single biomarkers, also the ratio of the biomarkers to KLK3 was determined using the Delta DeltaCT method (ΔΔCT).

RNA Extraction

Automated nucleic acid isolation was carried out using the MagNA Pure 96 Instrument (Roche). In duplicate, RNA was extracted from 1 ml of processed urine specimens with the DNA and Viral NA Large volume kit (Roche) using the Pathogen Universal protocol according to the manufacturer's instructions. Purified RNA (50 µl) from each duplicate extraction was transferred to one well in an 8-well strip (Ambion) and mixed (100 µL total volume). The 8-well strips were stored at −80° C. prior to RT-qPCR determination.

One Step Reverse Transcription Quantitative PCR (RT-qPCR)

A 4-gene RT-qPCR test for use with post-DRE whole urine specimen was used. The test is based on Taqman® PCR technology combined with the absolute quantification of target RNA sequences of KLK3, HOXC6, DLX1, TDRD1 and HOXC4. The components for the test include a singleplex mastermix for the 5 targets, a calibrator and a RT-control. The calibrator consists of a multi-target-plasmid containing the target sequences and the RT-control is a mix of in vitro transcribed (IVT) RNA from the targeted sequences. Per test run, 10,000 copies of the multi-target-plasmid (Cal $10^4$) and IVT RNA were used as positive reference controls. A separate RT-qPCR assay was developed to measure PCA3 transcripts in urine based on the same principle as described above. [assay characteristics not shown]

Quantification of the RNA

For each transcript, 14 µl of RNA specimen or control was mixed with 6 µl Mastermix in a single well of a LightCycler® 480 multiwell plate (Roche). The 20 µl reaction was reverse-transcribed and amplified in a LightCycler® 480 II system (Roche) according to the manufacturer's instructions of the prototype amplification kit. The levels of gene expression were calculated with the Abs Quant/2nd Derivative (high confidence) crossing point (Cp) method implemented by the LightCycler® 480 software version 1.5.0 (Roche). The Cross point cycle (Cp; also known as Threshold cycle $C_t$) is the cycle number at which the fluorescence signal crosses the threshold of the baseline in the qPCR. The Cp value inversely correlates with the initial concentration of the mRNA, e.g. the lower the Cp the higher the gene expression in the sample. The Cp values and copy numbers of the single target genes were determined and the ratio of the target gene versus the reference gene (KLK3) was calculated to normalize the qPCR results, using the Delta DeltaCp method ($\Delta\Delta Cp$):

$$\text{Ratio} = 2\left(\left(AvgCp_{(Cal10^4)_{target}} - Cp_{(sample)_{target}}\right) - \left(AvgCp_{(Cal10^4)_{reference}} - Cp_{(sample)_{reference}}\right)\right) \times 10.000$$

Evaluation Assay Performance

Assay performance was evaluated during the in-study validation. In each run a negative nucleic acid isolation control (NAI−) and a negative template control (NTC) were included. The Cp values for the negative controls were required to be negative for each of the RT-qPCR assays. KLK3 was used as an endogenous positive nucleic acid isolation control and was required to be positive in each urine sample. In each RT-qPCR run the positive reference controls were included and monitored. They were required to be within a 30% CV compared to the reference value. The assays for HOXC6, DLX1, TDRD1, HOXC4, KLK3 and PCA3 met these acceptance criteria parameters in both clinical trials.

Statistical Analysis

Statistical analysis was performed with SPSS® version 20.0. Two-sided p-values of <0.05 were considered to indicate statistical significance. Nonparametric statistical tests were used and the distribution was given in median and range (first quartile (Q1)-third quartile (Q3)). The expression levels of the biomarkers were compared with the outcome of the prostate biopsies. Backward logistic regression analysis was used to test if the novel biomarkers had independent additional predictive value. The test performance characteristics, area under the curve (AUC) of the Receiver Operating Characteristic (ROC) curve and corresponding 95% confidence intervals (CI) of the final model were determined. Bootstrapping analysis was performed for internal validation of the models and to test the robustness of the models in predicting high-grade PCa upon biopsy.

Results

Patient Characteristics

In total 905 urine samples were collected in two independent prospective clinical trials (cohort A: n=519; cohort B: n=386). Patient characteristics are shown in Table 1. In cohort A 212 of 519 men (41%) had a positive biopsy outcome of which 109 men (51%) had high-grade PCa (GS≥7). In cohort B this was 181 of 386 men (47%), and 91 (50%) with high-grade PC, respectively. There was a statistically significant difference in the number of patients having previous biopsies (<0.01), with a higher percentage in cohort A as compared to cohort B. No other statistically significant differences in baseline characteristics were found between the cohorts.

TABLE 1

Patient characteristics

| Descriptives | Cohort A (n = 519) median (range)/n (%) | Cohort B (n = 386) median (range)/n (%) | p-value |
|---|---|---|---|
| Age | 65 (44-86) | 65 (39-84) | 0.28[a] |
| sPSA (ng/ml) | 7.4 (5.5-11.1) | 7.3 (5.2-10.9) | 0.29[a] |
| PCa in family | 91 (18%) | 74 (19%) | 0.53[b] |
| No previous biopsies | 410 (79%) | 342 (89%) | <0.01[b] |
| TRUS prostate volume (cc) | 48 (15-200) | 45 (15-270) | 0.08[a] |
| PCa upon biopsy* | 214 (41%) | 181 (47%) | 0.09[b] |
| GS ≤6 | 103 (49%) | 90 (50%) | |
| GS 7 | 58 (27%) | 52 (29%) | |
| GS 8-10 | 51 (24%) | 39 (22%) | |

DRE = Digital Rectal Examination,
TRUS = TransRectal UltraSound,
GS = Gleason score
*from 2 subjects the total GS could not be determined, at least a Gleason 4 component was present.
[a]Mann-Whitney U test, significance level <0.05;
[b]Chi-square test, significance level <0.05

Biomarker Characteristics

All 905 urine samples contained detectable levels of the prostate-specific transcript KLK3 The median biomarker levels (and Cp values) were within comparable ranges, with the note that a lower Cp value means higher transcript/RNA (Table 2).

TABLE 2

Biomarker characteristics

| | Cohort A (n = 519) | | Cohort B (n = 386) | |
|---|---|---|---|---|
| | Copy numbers | Cp value | Copy numbers | Cp value |
| KLK3 | 19149 (6693-50691) | 25.3 (23.8-26.8) | 20627 (9073-45958) | 25.0 (23.8-26.2) |
| PCA3 | 2140 (572-8062) | 28.1 (26.1-30.0) | 2247 (633-8206) | 28.0 (26.1-30.0) |
| HOXC6 | 96 (36-229) | 34.2 (32.8-35.7) | 100 (37-247) | 34.1 (32.7-35.6) |
| DLX1 | 15 (5-44) | 34.9 (32.7-36.2) | 13 (4-29) | 35.7 (34.6-36.7) |

TABLE 2-continued

| | Biomarker characteristics | | | |
|---|---|---|---|---|
| | Cohort A (n = 519) Copy numbers | Cp value | Cohort B (n = 386) Copy numbers | Cp value |
| TDRD1 | 73 (29-189) | 32.0 (30.4-33.3) | 64 (25-135) | 32.8 (31.7-34.0) |
| HOXC4 | 76 (34-186) | 33.0 (31.7-34.2) | 79 (31-202) | 32.9 (31.5-34.2) | median (Q1-Q3)
Cp = crossing point,
Q1-Q3 = inter quartile range

Figure 2:
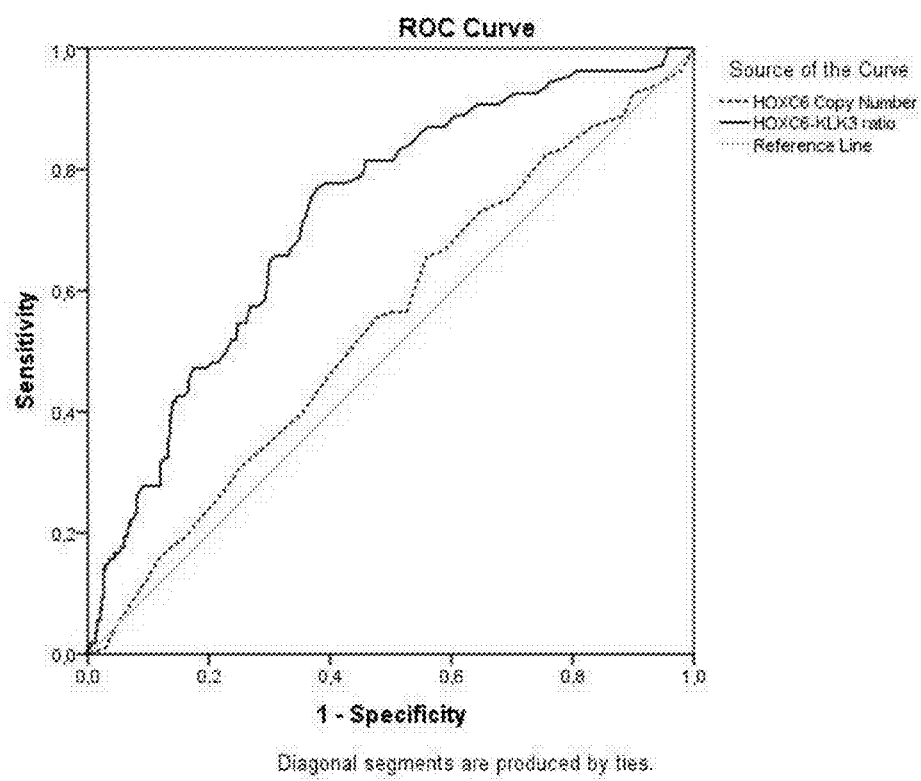
FIG. 2: shows the ROC curves for the prediction of high grade PCa upon prostate biopsy: (1) HOXC6/KLK3 ratio (black solid line; AUC 0.72 [95% CI: 0.67-0.78]); (2) HOXC6 copy number (grey dotted line; AUC 0.54 [95% CI: 0.48-0.61])

Performance of the Expression of the Single Target Genes Compared to the Target Gene/KLK3 Ratio To determine the value of normalization of the expression of the target genes with KLK3 expression for diagnosis of high-grade PCa in whole urine, the AUCs were compared in cohort A. Using the ratio of the target genes and KLK3 resulted in an enormous increase of the AUC as is shown for HOXC6 and DLX1 in FIGS. 1 and 2. For HOXC6 the AUC increased from 0.54 to 0.72 for the HOXC6/KLK3 ratio [95% CI: 0.67-0.78]. For DLX1 alone the AUC was 0.51 and for the DLX1/KLK3 ratio 0.64 [95% CI: 0.58-0.71].

Selection of a Predictive Model for the Diagnosis of High-Grade PCa Upon Biopsy

To develop a predictive model the 519 samples derived from cohort A were used. To compare the utility of the biomarkers to predict high-grade (GS≥7) PCa upon biopsy, a threshold of ≈90% sensitivity was chosen. The cut-off at ≈90% sensitivity was determined, as were the AUC, sensitivity, specificity, NPV, and PPV for each biomarker (Table 3). Of the single markers, HOXC6 had the highest AUC (AUC=0.73 [95% CI: 0.68-0.79]) and the highest specificity of 33% at 91% sensitivity.

Biomarker levels of HOXC6 and HOXC4 were observed to strongly correlate with each other (Pearson correlation (R2) of 0.80) indicating that they would not complement each other. To determine whether DLX1 and TDRD1 could complement the performance of either HOXC6 or HOXC4, models were based on the sum of the ratios. Using a cut-off of 27.5, the combination HOXC6+DLX1 had the best performance with an AUC of 0.76 (95% CI: 0.71-0.81). The addition of other markers to this model did not result in an improvement of the test performance (Table 3).

The combination of HOXC6+DLX1 ratios had the highest AUC overall for prediction of high-grade PCa upon biopsy, this model will be referred to as the HOXC6-DLX1 score.

Bootstrap Analysis

Bootstrap resampling was used as an internal validation of the models. After 100 bootstrap replications, HOXC6 and DLX1 significantly improved the predictive accuracy for high-grade PCa in 97% and 98% of the bootstrap samples, respectively. In the biomarker models based on HOXC6, TDRD1 improved the accuracy in 38% of the bootstrap samples. Overall, the models based on HOXC6 had the highest AUCs, and the highest AUC overall was obtained for the model based on the sum of HOXC6+DLX1. Therefore, the combination of HOXC6+DLX1 was the best predictive model for identification of high-grade PCa upon biopsy, this model will be referred to as the HOXC6-DLX1 score.

Informative Rate

KLK3 was used as a measure for the presence of prostate derived transcripts and the expression level was about 1000 fold higher than of HOXC6 and DLX1 (Table 2). To exclude false negative outcomes, a urine sample with HOXC6-DLX1 score≤27.5 needed to have at least 10,000 copies of KLK3. As this KLK3 threshold was set, 27 samples in cohort A were marked as non-informative, resulting in 492 informative samples (95%). In cohort B, 15 samples were marked as non-informative, resulting in 371 informative samples (96%).

Clinical Performance of the HOXC6-DLX1 Score for Prediction of High-Grade PCa

To demonstrate the predictive accuracy in cohort A (n=492) ROC curves were generated for the HOXC6-DLX1 score and PCA3 using high-grade PCa upon biopsy as

TABLE 3

Biomarker models used for the development with cut-off and clinical performance.

| Model | Cut-off | AUC | Se (%) | Sp (%) | NPV (%) | PPV (%) |
|---|---|---|---|---|---|---|
| PCA3 | 35.0 | 0.65 | 91 | 20 | 89 | 23 |
| TDRD1 | 1.0 | 0.69 | 90 | 11 | 80 | 21 |
| DLX1 | 0.5 | 0.65 | 83 | 16 | 79 | 21 |
| HOXC4 | 15.5 | 0.64 | 91 | 22 | 90 | 23 |
| HOXC4 + DLX1 | 26.5 | 0.70 | 91 | 31 | 93 | 25 |
| HOXC4 + TDRD1 | 50.5 | 0.72 | 91 | 30 | 93 | 25 |
| HOXC4 + DLX1 + TDRD1 | 57.5 | 0.73 | 91 | 31 | 93 | 26 |
| HOXC6 | 19.5 | 0.73 | 91 | 33 | 93 | 26 |
| HOXC6 + DLX1 | 27.5 | 0.76 | 91 | 36 | 94 | 27 |
| HOXC6 + TDRD1 | 50.5 | 0.74 | 91 | 35 | 94 | 27 |
| HOXC6 + DLX1 + TDRD1 | 55.5 | 0.74 | 91 | 34 | 93 | 26 |
| HOXC6 + HOXC4 + DLX1 + TDRD1 | 85.5 | 0.74 | 91 | 33 | 93 | 26 |

Figure 3:
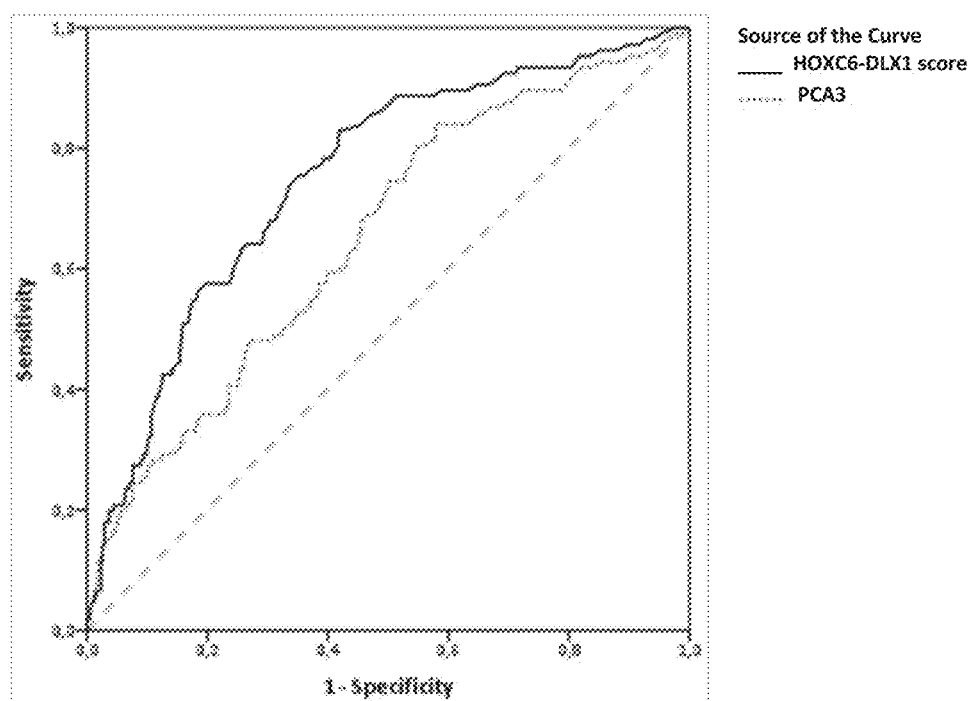
FIG. 3: shows the ROC curves for the prediction of high grade PCa upon prostate biopsy: (1) HOXC6-DLX1 score (black solid line; AUC 0.75 [95% CI: 0.70-0.80]); (2) PCA3 (grey dotted line; AUC 0.65 [95% CI: 0.59-0.71])

AUC = Area Under the Curve.
Se = Sensitivity.
Sp = Specificity.
NPV = Negative Predictive Value.
PPV = Positive Predictive Value.

clinical outcome (FIG. 3). The HOXC6–DLX1 score (AUC 0.75 [95% CI: 0.70-0.80]) outperformed PCA3 (AUC 0.65 [95% CI: 0.59-0.71]). The specificity of the HOXC6–DLX1 score was higher compared to PCA3, 32% versus 19%.

Using the 371 informative samples of cohort B, the predictive accuracy of the HOXC6–DLX1 score was independently validated. The clinical performance of the HOXC6–DLX1 score in cohort B (AUC 0.73 [95% CI: 0.67-0.78]) was comparable to its performance in cohort A (AUC 0.75). Moreover, the sensitivity remained 92% and the specificity increased to 37%, versus 32% in cohort A (Table 4).

TABLE 4

Clinical performance of the HOXC6-DLX1 score

| HOXC6-DLX1 score | Cohort A (n = 492) | Cohort B (n = 371) |
|---|---|---|
| AUC | 0.75 | 0.73 |
| (95% CI) | (0.70-0.80) | (0.67-0.78) |
| Sensitivity | 92% | 92% |
| Specificity | 32% | 37% |
| NPV | 93% | 94% |
| PPV | 27% | 32% |

AUC = Area Under the Curve, NPV = Negative Predictive Value, PPV = Positive Predictive Value.

HOXC6–DLX1 Scores in Relation to Biopsy Gleason Scores

Figure 4:
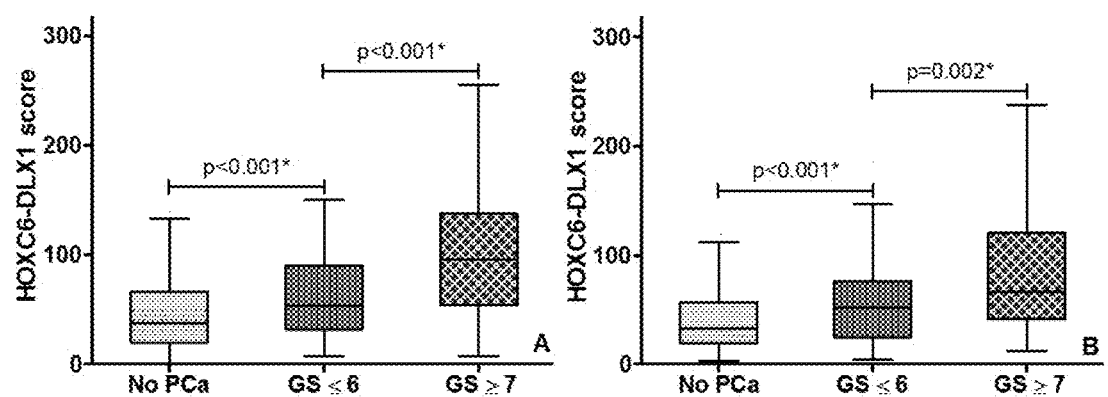
FIG. 4: shows the HOXC6-DLX1 score in relation to the Gleason score in cohort A (A) and cohort B (B). Mann-Whitney U test, significance level $p<0.05$.

In cohort A 286 men (58%) had no PCa upon prostate biopsy, 98 men (20%) had GS≤6, and 108 men (22%) had GS≥7. In cohort B this was 196 (53%), 86 (23%), and 89 (24%), respectively. The HOXC6–DLX1 score was significantly correlated with the Gleason score upon biopsy in both cohorts A and B (FIG. 4).

Performance of the HOXC6–DLX1 Score in the sPSA 'Grey Zone'

Figure 5:
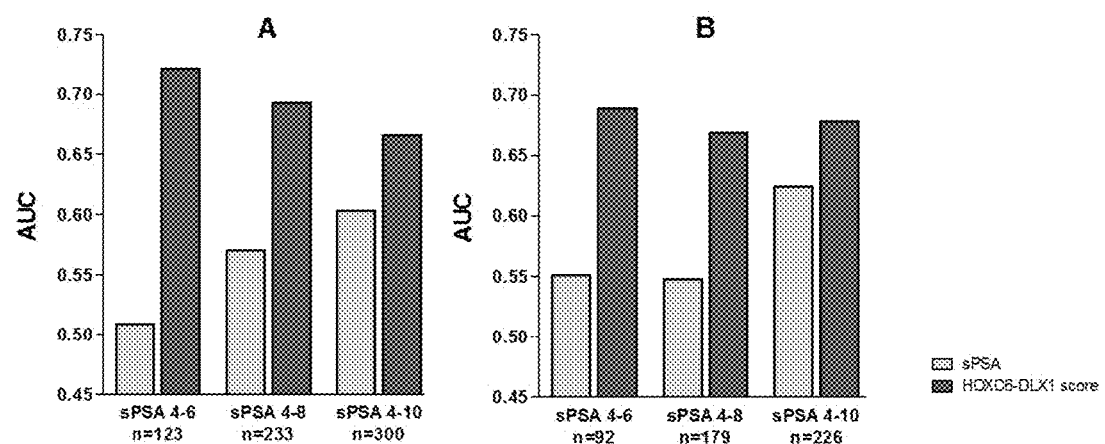
FIG. 5: shows the predictive accuracy (AUC) of the HOXC6-DLX1 score and sPSA for the detection of high grade PCa at low sPSA subgroups for cohort A (A) and cohort B (B).

To determine the additional value in the sPSA 'grey zone' (sPSA 4.0-10.0 ng/ml), the AUCs of the HOXC6–DLX1 score for diagnosis of high-grade PCa were compared to the AUCs of sPSA in low sPSA subgroups (FIG. 5). The AUCs of the HOXC6–DLX1 score ranged from 0.68 to 0.71 in cohort A. The AUCs of sPSA at lower sPSA cut-offs decreased to 0.52. In cohort B the AUCs of the HOXC6–DLX1 score ranged from 0.69 to 0.71, whereas the AUC of sPSA decreased to 0.55 in the lowest sPSA group.

Discussion

In many studies new promising PCa-specific biomarkers have been identified, however, to date only few biomarkers have reached clinical practice. The challenge is to independently validate the performance of the biomarkers in a clinical cohort. In the present example, a multicenter study a model is outlined using promising biomarkers. The HOXC6–DLX1 score had the best predictive value for high-grade PCa upon prostate biopsy and was validated in an independent cohort.

To prevent false negative samples in this study, a threshold for KLK3 level (<10,000 copies) was established for samples with a HOXC6–DLX1 score≤27.5. Another explanation for a false negative HOXC6–DLX1 test could be too little tumor content released into the urine, due to small tumor size or tumor location (base of the prostate, which cannot be reached by DRE). Urine samples were collected using the Gen-Probe (Hologic) urine tubes.

Currently, no test is completely accurate in detecting PCa. Defining an optimal cut-off score will always be a compromise between sensitivity and specificity, depending on what risk of missing significant tumors is clinically acceptable. In this example, a sensitivity of 90% for prediction of high-grade PCa upon prostate biopsy was chosen for model development.

In cohort A 131 (27%) subjects had a HOXC6–DLX1 score of ≤27.5 and in cohort B 111 (30%) of men. Of these men 9 (7%), respectively 7 (6%) had high-grade PCa upon biopsy. In total (n=863), 242 biopsies (28%) could have been avoided if the HOXC6–DLX1 score would have been performed, with the risk of missing 7% high-grade PCa.

Nowadays, using sPSA with threshold 4 ng/ml in PCa detection also a certain percentage of the high-grade PCa is missed. In the Prostate Cancer Prevention Trial, diagnosis of PCa is reported in 15.2% of men with a sPSA level of ≤4 ng/ml, of which 14.9% had a high-grade PCa (GS≥7). This risk was very low for patients with a sPSA level <1 ng/ml, but increased to 9.4% in patients with a sPSA between 3-4 ng/ml, i.e. one could conclude that the current accepted risk of missing significant cancers using sPSA is up to 9.4% when a threshold of 4 ng/ml is used, or 5.7% when a threshold of 3 ng/ml is used. Using a cut-off of 27.5 for the HOXC6–DLX1 score, 4% of patients with high-grade PCa in the sPSA range between 4-10 mg/ml would be missed, which is lower than the risk profile for a sPSA threshold between 2-4 ng/ml (7.2%). Given the characteristics of the HOXC6–DLX1 score, the risk to miss high-grade cancer in patients with sPSA values <4 ng/ml might be further reduced. Patients with sPSA levels ≤4 ng/ml would be an interesting population to study the additional value of the HOXC6–DLX1 urine test.

CONCLUSION

The HOXC6–DLX1 urine test is a powerful tool for prediction of high-grade PCa upon prostate biopsy and could therefore be used in decision making, reducing the number of unnecessary prostate biopsies and potential overtreatment.

REFERENCES

[1] Torre L A, Bray F, Siegel R L, Ferlay J, Lortet-Tieulent J, Jemal A. Global cancer statistics, 2012. CA: a cancer journal for clinicians. 2015; 65:87-108.
[2] Draisma G, Etzioni R, Tsodikov A, Mariotto A, Wever E, Gulati R, et al. Lead time and overdiagnosis in prostate-specific antigen screening: importance of methods and context. Journal of the National Cancer Institute. 2009; 101:374-83.
[3] Welch H G, Albertsen P C. Prostate cancer diagnosis and treatment after the introduction of prostate-specific antigen screening: 1986-2005. Journal of the National Cancer Institute. 2009; 101:1325-9.
[4] Albertsen P C, Hanley J A, Fine J. 20-year outcomes following conservative management of clinically localized prostate cancer. Jama. 2005; 293:2095-101.
[5] Groskopf J, Aubin S M, Deras I L, Blase A, Bodrug S, Clark C, et al. APTIMA PCA3 molecular urine test: development of a method to aid in the diagnosis of prostate cancer. Clinical chemistry. 2006; 52:1089-95.
[6] Gittelman M C, Hertzman B, Bailen J, Williams T, Koziol I, Henderson R J, et al. PCA3 molecular urine test as a predictor of repeat prostate biopsy outcome in men with previous negative biopsies: a prospective multicenter clinical study. The Journal of urology. 2013; 190:64-9.
[7] Bussemakers M J, van Bokhoven A, Verhaegh G W, Smit F P, Karthaus H F, Schalken J A, et al. DD3: a new prostate-specific gene, highly overexpressed in prostate cancer. Cancer research. 1999; 59:5975-9.
[8] Hessels D, Klein Gunnewiek J M, van Oort I, Karthaus H F, van Leenders G J, van Balken B, et al. DD3(PCA3)-based molecular urine analysis for the diagnosis of prostate cancer. European urology. 2003; 44:8-15; discussion-6.
[9] Auprich M, Chun F K, Ward J F, Pummer K, Babaian R, Augustin H, et al. Critical assessment of preoperative urinary prostate cancer antigen 3 on the accuracy of prostate cancer staging. European urology. 2011; 59:96-105.
[10] Marks L S, Fradet Y, Deras I L, Blase A, Mathis J, Aubin S M, et al. PCA3 molecular urine assay for prostate cancer in men undergoing repeat biopsy. Urology. 2007; 69:532-5.
[11] Ploussard G, Haese A, Van Poppel H, Marberger M, Stenzl A, Mulders P F, et al. The prostate cancer gene 3 (PCA3) urine test in men with previous negative biopsies: does free-to-total prostate-specific antigen ratio influence the performance of the PCA3 score in predicting positive biopsies? BJU international. 2010; 106:1143-7.
[12] Leyten G H, Hessels D, Smit F P, Jannink S A, de Jong H, Melchers W J, et al. Identification of a Candidate Gene Panel for the Early Diagnosis of Prostate Cancer. Clinical cancer research: an official journal of the American Association for Cancer Research. 2015; 21:3061-70.
[13] Schmittgen T D, Livak K J. Analyzing real-time PCR data by the comparative C(T) method. Nature protocols. 2008; 3:1101-8.
[14] Hendriks R J, Dijkstra S, Jannink S A, Steffens M G, Van Oort I M, Mulders P F A, et al. Comparative analysis of prostate cancer specific biomarkers PCA3 and ERG in whole urine, urinary sediments and exosomes. Submitted. 2015.
[15] Thompson I M, Pauler D K, Goodman P J, Tangen C M, Lucia M S, Parnes H L, et al. Prevalence of prostate cancer among men with a prostate-specific antigen level< or =4.0 ng per milliliter. The New England journal of medicine. 2004; 350:2239-46.
[16] Thompson I M, Ankerst D P, Chi C, Goodman P J, Tangen C M, Lucia M S, et al. Assessing prostate cancer risk: results from the Prostate Cancer Prevention Trial. Journal of the National Cancer Institute. 2006; 98:529-34.
[17] Wolters T, van der Kwast T H, Vissers C J, Bangma C H, Roobol M, Schroder F H, et al. False-negative prostate needle biopsies: frequency, histopathologic features, and follow-up. The American journal of surgical pathology. 2010; 34:35-43.
[18] Roehl K A, Antenor J A, Catalona W J. Serial biopsy results in prostate cancer screening study. The Journal of urology. 2002; 167:2435-9.
[19] Hoeks C M, Barentsz J O, Hambrock T, Yakar D, Somford D M, Heijmink S W, et al. Prostate cancer: multiparametric MR imaging for detection, localization, and staging. Radiology. 2011; 261:46-66.
[20] Tonttila P P, Lantto J, Paakko E, Piippo U, Kauppila S, Lammentausta E, et al. Prebiopsy Multiparametric Magnetic Resonance Imaging for Prostate Cancer Diagnosis in Biopsy-naive Men with Suspected Prostate Cancer Based on Elevated Prostate-specific Antigen Values: Results from a Randomized Prospective Blinded Controlled Trial. European urology. 2015, http://dx.doi.org/10.1016/j.eururo.2015.05.024
[21] Baco E, Rud E, Eri L M, Moen G, Vlatkovic L, Svindland A, et al. A Randomized Controlled Trial To Assess and Compare the Outcomes of Two-core Prostate Biopsy Guided by Fused Magnetic Resonance and Transrectal Ultrasound Images and Traditional 12-core Systematic Biopsy. European urology. 2015, http://dx.doi.org/10.1016/j.eururo.2015.03.041
[22] Budaus L, Leyh-Bannurah S R, Salomon G, Michl U, Heinzer H, Huland H, et al. Initial Experience of Ga-PSMA PET/CT Imaging in High-risk Prostate Cancer Patients Prior to Radical Prostatectomy. European urology. 2015 http://dx.doi.org/10.1016/j.eururo.2015.06.010.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A method comprising:
    (a) reacting a nucleic acid isolated from urine of a patient with a reagent composition that comprises polynucleotide reagents for detecting levels of DLX1 mRNA, HOXC6 mRNA, and KLK3 mRNA in the nucleic acid sample; and
    (b) detecting the levels of DLX1 mRNA, HOXC6 mRNA, and KLK3 mRNA in the nucleic acid sample, wherein the polynucleotide reagents for detecting levels of DLX1 mRNA, HOXC6 mRNA, and KLK3 mRNA in the nucleic acid sample comprise a pair of oligonucleotides for amplifying reverse transcribed mRNA for each of the genes DLX1, HOXC6 and KLK3.

2. The method according to claim 1, wherein the reagent composition further comprises polynucleotide reagents for detecting levels of TDRD1 mRNA in the nucleic acid sample, and the method further comprises detecting the levels of TDRD1 mRNA in the nucleic acid sample.

3. The method according to claim 1, further comprising performing a biopsy of prostate tissue from the patient.

4. The method according to claim 1, further comprising administering treatment for aggressive prostate cancer.

5. The method according to claim 4, wherein the treatment for prostate cancer comprises performing surgery, administering radiation therapy, administering radiopharmaceutical therapy, administering hormone therapy, administering chemotherapy, administering biologic therapy, administering bisphosphonate therapy, administering cryotherapy, administering high-intensity focused ultrasound therapy, administering proton beam radiation therapy, or a combination thereof.

6. The method according to claim 1, further comprising:
(a) reacting a serum sample from the patient with a reagent composition that comprises components for detecting levels of prostate-specific antigen (sPSA) in the serum sample;
(b) detecting the levels of sPSA in the serum sample.

7. The method accordingly to claim 1, wherein the urine sample is a first voided urine sample collected after a digital rectal examination.

8. The method accordingly to claim 1, further comprising isolating the nucleic acid sample from urine of the patient.

* * * * *